(12) United States Patent
Brace et al.

(10) Patent No.: US 11,529,238 B2
(45) Date of Patent: Dec. 20, 2022

(54) SLEEVE FOR PERCUTANEOUS DEVICE AND METHODS OF PRODUCTION AND USE THEREOF

(71) Applicant: DePuy Synthes Products, LLC, Raynham, MA (US)

(72) Inventors: Michael Brace, West Chester, PA (US); Hetal Baman, West Chester, PA (US); Richard Healey, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 769 days.

(21) Appl. No.: 16/569,524

(22) Filed: Sep. 12, 2019

(65) Prior Publication Data

US 2021/0077261 A1 Mar. 18, 2021

(51) Int. Cl.
*A61B 17/66* (2006.01)
*A61F 2/30* (2006.01)

(52) U.S. Cl.
CPC .......... *A61F 2/30907* (2013.01); *A61B 17/66* (2013.01); *A61F 2002/30003* (2013.01); *A61F 2002/30546* (2013.01); *A61F 2002/30667* (2013.01); *A61F 2002/30845* (2013.01); *A61F 2002/30919* (2013.01)

(58) Field of Classification Search
CPC .... A61F 2/30907; A61F 15/006; A61B 17/60; A61B 17/62–663; A61B 2017/681
See application file for complete search history.

(56) References Cited

U.S. PATENT DOCUMENTS

| 5,281,221 A | 1/1994 | Tadych |
|---|---|---|
| 5,906,600 A | 5/1999 | Bähr |
| 8,840,611 B2 | 9/2014 | Mullaney et al. |
| 2003/0036761 A1 | 2/2003 | Smothers et al. |

FOREIGN PATENT DOCUMENTS

| CN | 2282410 Y | 5/1998 |
|---|---|---|
| CN | 103393492 A | 11/2013 |
| DE | 3729253 A1 | 3/1989 |
| IN | 2008CH00979 A | 4/2008 |
| WO | 9844967 | 10/1998 |

*Primary Examiner* — Brian A Dukert
(74) *Attorney, Agent, or Firm* — Dunlap Codding, P.C.

(57) ABSTRACT

A sleeve for use with a percutaneous, external fixation device is disclosed, wherein the sleeve includes a sleeve body with an interior space in which the percutaneous device can be disposed, a flange that extends at a substantially perpendicular angle to the sleeve body, and a cutting edge extending from the sleeve body below the flange. The cutting edge is designed for placement in contact with the skin adjacent to the percutaneous device so as to define a leading edge thereof in a primary anticipated direction of migration of the percutaneous device. Kits and assemblies that include sleeves and percutaneous devices are also disclosed. Further disclosed are methods of reducing tension in a patient's skin following placement of the percutaneous device via use of the sleeve, as well as methods of adjusting and readjusting the assembly upon placement.

38 Claims, 5 Drawing Sheets

SLEEVE FOR PERCUTANEOUS DEVICE AND METHODS OF PRODUCTION AND USE THEREOF

CROSS REFERENCE TO RELATED APPLICATIONS/INCORPORATION BY REFERENCE STATEMENT

Not Applicable.

STATEMENT REGARDING FEDERALLY SPONSORED RESEARCH OR DEVELOPMENT

Not Applicable.

BACKGROUND

Percutaneous devices, such as (but not limited to) pins, screws, and wires, are commonly used in orthopedic procedures to stabilize and/or correct fractures, injuries, and defects. Particular examples of percutaneous devices include (but are not limited to) skeletal traction pins, percutaneous fracture pinning, and external fixation devices. However, tension is created in the skin adjacent to the percutaneous devices at the insertion sites thereof, and this tension can decrease blood supply and lead to necrosis of the surrounding tissue, thus acting as a 'magnet' for infection at the insertion site.

For example, external fixation of bone fractures commonly involves the long-term use of orthopedic pins inserted into the bone fragments and fixed to an external structure. The pins stress the skin around them during bone distraction and/or healing (or simply in response to patient movement), often leading to the cutting or tearing of pin tracts in the skin, along with the subsequent infection associated therewith. Indeed, one study reported site infection as the most common complication of external fixation, with an 11.3% to 100% infection rate in the study group (Kazmers et al., (2016) *Strat Traum Limb Recon*, 11:75-85).

Currently, clinicians recommend a variety of techniques to try to prevent pin tract infection, including local antiseptics and regular pin site cleaning. Despite aggressive treatments, however, pin tract infection is still the most common complication of external fixation. In addition, the risk of pin tract infection increases with time; the longer an external fixation pin remains in place, the higher the risk of infection and the more severe the infections become. With more recently developed surgical treatments such as distraction osteogenesis, external fixation pins can remain in place for many months, and the success of these distraction osteogenesis procedures depends upon the ability to maintain the fixation pins infection-free for long periods. Pin tract infection can decrease the stability of the fixator pin-bone interface, which creates an unsuitable environment for optimal bone healing and can lead to pin loosening, fracture nonunion, and chronic osteomyelitis (Ferreira and Marais (2012) *Strategies Trauma Limb Reconstr*, 7(2): 67-72). While soft tissue infection can often be treated effectively with oral antibiotics and local skin treatment, deeper bone infection typically requires removal of percutaneous pins or abandonment of external fixation altogether.

Therefore, there is a need in the art for new and improved devices and methods of using same around the insertion sites of percutaneous devices to minimize the amount of cutting/tearing of skin that occurs in response to bone distraction, healing, or patient movement, thereby reducing the risk of infection around the insertion sites. It is to such devices, as well as methods of producing and using same, that the present disclosure is directed.

DETAILED DESCRIPTION

Before explaining at least one embodiment of the present disclosure in detail by way of exemplary language and results, it is to be understood that the present disclosure is not limited in its application to the details of construction and the arrangement of the components set forth in the following description. The present disclosure is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the medical procedures and techniques of, surgery, anesthesia, wound healing, and infectious control described herein are those well-known and commonly used in the art. Standard techniques are used for infection diagnostic and therapeutic applications.

All patents, published patent applications, and non-patent publications mentioned in the specification are indicative of the level of skill of those skilled in the art to which the present disclosure pertains. All patents, published patent applications, and non-patent publications referenced in any portion of this application are herein expressly incorporated by reference in their entirety to the same extent as if each individual patent or publication was specifically and individually indicated to be incorporated by reference.

All of the articles, compositions, kits, and/or methods disclosed herein can be made and executed without undue experimentation in light of the present disclosure. While the articles, compositions, kits, and/or methods have been described in terms of particular embodiments, it will be apparent to those of skill in the art that variations may be applied to the articles, compositions, kits, and/or methods and in the steps or in the sequence of steps of the methods described herein without departing from the concept, spirit, and scope of the present disclosure. All such similar substitutions and modifications apparent to those skilled in the art are deemed to be within the spirit, scope, and concept of the present disclosure as defined by the appended claims.

As utilized in accordance with the present disclosure, the following terms, unless otherwise indicated, shall be understood to have the following meanings:

The use of the term "a" or "an" when used in conjunction with the term "comprising" in the claims and/or the specification may mean "one," but it is also consistent with the meaning of "one or more," "at least one," and "one or more than one." As such, the terms "a," "an," and "the" include plural referents unless the context clearly indicates otherwise. Thus, for example, reference to "a compound" may refer to one or more compounds, two or more compounds, three or more compounds, four or more compounds, or greater numbers of compounds. The term "plurality" refers to "two or more."

The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z.

The use of ordinal number terminology (i.e., "first," "second," "third," "fourth," etc.) is solely for the purpose of differentiating between two or more items and, unless explicitly stated otherwise, is not meant to imply any sequence or order or importance to one item over another or any order of addition, for example.

The use of the term "or" in the claims is used to mean an inclusive "and/or" unless explicitly indicated to refer to alternatives only or unless the alternatives are mutually exclusive. For example, a condition "A or B" is satisfied by any of the following: A is true (or present) and B is false (or not present), A is false (or not present) and B is true (or present), and both A and B are true (or present).

As used herein, any reference to "one embodiment," "an embodiment," "some embodiments," "one example," "for example," or "an example" means that a particular element, feature, structure, or characteristic described in connection with the embodiment is included in at least one embodiment. The appearance of the phrase "in some embodiments" or "one example" in various places in the specification is not necessarily all referring to the same embodiment, for example. Further, all references to one or more embodiments or examples are to be construed as non-limiting to the claims.

Throughout this application, the term "about" is used to indicate that a value includes the inherent variation of error for a composition/apparatus/device, the method being employed to determine the value, or the variation that exists among the study subjects. For example, but not by way of limitation, when the term "about" is utilized, the designated value may vary by plus or minus twenty percent, or fifteen percent, or twelve percent, or eleven percent, or ten percent, or nine percent, or eight percent, or seven percent, or six percent, or five percent, or four percent, or three percent, or two percent, or one percent from the specified value, as such variations are appropriate to perform the disclosed methods and as understood by persons having ordinary skill in the art.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps. For example, a process, method, article, or apparatus that comprises a list of elements is not necessarily limited to only those elements but may include other elements not expressly listed or inherently present therein.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, when associated with a particular event or circumstance, the term "substantially" means that the subsequently described event or circumstance occurs at least 80% of the time, or at least 85% of the time, or at least 90% of the time, or at least 95% of the time. The term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

As used herein, the phrases "associated with" and "coupled to" include both direct association/binding of two moieties to one another as well as indirect association/binding of two moieties to one another. Non-limiting examples of associations/couplings include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety, for example.

As used herein, the term "patient" or "subject" is meant to include all organisms, whether alive or dead, including any species having soft tissues and bones. For example, a system according to the inventive concepts disclosed herein may be applied to the skin of a living human, horse, cow, sheep, cat, dog, and the like.

The term "agent" as used herein refers to a chemical compound, a mixture of chemical compounds, a biological macromolecule, or an extract made from biological materials that is utilized for a desired purpose. A "therapeutic agent" or "pharmaceutical agent" refers to an agent that may be administered to bring about a therapeutic and/or prophylactic/preventative effect.

Certain non-limiting embodiments of the present disclosure are directed to a sleeve for a percutaneous device. The sleeve includes a sleeve body, a flange, and a cutting edge. The sleeve body is at least partially hollow and may have any shape or dimension that allows the sleeve body to function in accordance with the present disclosure. In certain non-limiting embodiments, the sleeve body has a substantially tubular shape; however, the sleeve may have any other shapes disclosed or otherwise contemplated herein.

The sleeve body has an upper end, an open lower end, an outer surface, and an inner surface that defines an interior receiving space that extends from the open lower end; the interior receiving space is designed for receiving a portion of a percutaneous device within at least a portion thereof. The flange separates the sleeve body into an upper portion and a lower portion. The flange has an upper surface and a lower surface and extends at a substantially perpendicular angle from the outer surface of the sleeve body above the lower end thereof (so as to provide space for the cutting edge to be positioned between the flange and the lower end of the sleeve body, as discussed herein below); the flange is also designed to extend in a direction substantially parallel to the skin of the patient and is designed to be disposed upon a surface of the patient's skin.

The cutting edge has an upper end and a lower end and extends from a portion of the outer surface of the sleeve body below the flange; in this manner, the upper end of the cutting edge is substantially in contact with the lower surface of the flange. The cutting edge is designed for placement in contact with the skin adjacent to the percutaneous device and defines a leading edge thereof in a primary anticipated direction of migration. In addition, this configuration allows the flange to serve as a guard that ensures placement of the cutting edge within the skin and substantially protects any incision formed by the cutting edge from exposure to microorganisms.

The sleeves of the present disclosure provide various advantages over the prior art. As described herein above, the blunt sides of percutaneous devices stress the skin around them during patient movement, healing, and/or bone distraction, and the pressure zone so formed restricts blood supply while leading to cutting or tearing of the skin, thereby creating a significant opportunity for infection. In contrast, the cutting edge of the sleeves of the present disclosure provides a sharp, tapered point on the outer surface of the sleeve that dissects the skin and/or soft tissue surrounding the percutaneous device (to which the sleeve is attached) during movement of the percutaneous device, thereby removing the tension in the skin and promoting blood supply in the immediate area surrounding the percutaneous device; in this manner, the cutting of the skin/soft tissue is minimized to only the necessary amount required for the percutaneous device to move through the skin/soft tissue, while the risk of infection is also reduced. In addition, the flange of the sleeve functions as a guard to substantially protect the cutting edge and the percutaneous device insertion site from exposure to microorganisms (as the ability of microorganisms to penetrate into the incision/insertion site is reduced). Another advantage of the sleeves of the present disclosure is that the orientation of the cutting edge can be adjusted and readjusted, both with respect to the percutaneous device upon which the sleeve is attached (i.e., by varying the height at which the sleeve is disposed upon the percutaneous device) as well as with respect to orientation in an anticipated direction of migration/distraction. In this manner, the percutaneous device/sleeve assembly can be personalized to meet individual patient's needs and thus allow for development of individual patient treatment plans.

The individual portions of the sleeves disclosed herein may be formed of any material(s) that will allow the sleeve to function in accordance with the present disclosure. In certain non-limiting embodiments, at least a portion of the sleeve is formed of at least one substantially rigid material, such as (but not limited to) a metallic material, a polymeric material, or a combination thereof. In certain non-limiting embodiments, at least two of the components of the sleeve (i.e., the sleeve body, the flange, and the cutting edge) are integrally formed of the same material. In a particular (but non-limiting) embodiment, all three components of the sleeve are integrally formed of the same material. In an alternative embodiment, at least two or all three components of the sleeve (i.e., the sleeve body, the flange, and the cutting edge) are each formed of different materials.

The cutting edge of the sleeve may be provided with any configuration that minimizes the amount of cutting that is performed and also minimizes the risk of injury to a practitioner during handling of the sleeve. For example (but not by way of limitation), the cutting edge may be provided with a profile that varies from the upper end to the lower end thereof. That is, the cutting edge may have length and/or a width that decreases from the upper end to the lower end thereof. Alternatively (and/or in addition thereto), the profile of the cutting edge may taper to a blunt edge from the upper end to the lower end thereof. In yet another alternative embodiment, a diameter of an outer surface of a sleeve can decrease (as opposed to changing the actual length of the cutting edge). In addition, the lower end of the cutting edge may be substantially planar, or may be substantially convex or substantially concave, as desired.

In certain non-limiting embodiments, the lower end of the cutting edge is disposed substantially adjacent to the open lower end of the sleeve body. Alternatively, the cutting edge may not extend to the bottom of the sleeve body, and as such, the lower end of the cutting edge is disposed above the lower end of the sleeve body.

The sleeve may also include other elements that enhance the function of the sleeve and/or provide a mechanism for securing and/or aligning the sleeve. For example (but not by way of limitation), in certain embodiments, the sleeve may further include a securing element for releasably or permanently securing the sleeve to the percutaneous device. Alternatively (and/or in addition thereto), the sleeve may further include an alignment element for orienting the cutting edge in the primary anticipated direction of migration. Particular structures that function as securing elements and/or alignment elements are discussed in detail herein below and are also well known in the art. Therefore, no further description thereof is deemed necessary.

In another non-limiting embodiment, the sleeve may further include at least one agent disposed on at least a portion thereof. For example (but not by way of limitation), any portion of the sleeve (such as, but not limited to, at least a portion of the cutting edge and/or at least a portion of the sleeve body below the flange) may be provided with one or more agents disposed upon a portion of a surface thereof or incorporated/impregnated into at least a portion thereof. Non-limiting examples of agents that may be utilized in accordance with the present disclosure include therapeutic or pharmaceutical agents such as a medicament, a drug, a prodrug, an antimicrobial agent, a wound healing agent, an anti-inflammatory agent, combinations thereof, and the like. In addition, the sleeve may include differential coatings on one or more surfaces thereof, as desired. The agent(s) may be coated on the surface of the sleeve and/or incorporated within the material from which at least a portion of the sleeve is formed.

Any therapeutic or pharmaceutical agents known in the art or otherwise contemplatable by a person of ordinary skill in the art may be utilized in accordance with the present disclosure. For example (but not by way of limitation), the antimicrobial agent may be an antibacterial agent and/or an antifungal agent. Examples of antimicrobial and wound healing agents are well known in the art, and a wide variety thereof are commercially available. Therefore, it is well within the common abilities of a person having ordinary skill in the art to identify and select particular antimicrobial and wound healing agents that can be used in accordance with the present disclosure, given the particular uses for which the sleeves/assemblies are employed. As such, no further discussion thereon is deemed necessary. In addition, methods of applying coatings containing said agents are well known, as are methods of incorporating said agents into a polymer prior to extrusion thereof. Thus, no further description of application of said agents to the sleeves is deemed necessary.

In certain non-limiting embodiments, the upper end of the sleeve body may be closed, such that the interior receiving space does not extend from the lower end to the upper end thereof. Alternatively, the upper end of the sleeve body may be open such that the interior receiving space extends from the lower end to the upper end thereof; this configuration will allow a percutaneous device to extend above the open upper end of the sleeve body and thus extend through the sleeve, if desired.

Certain non-limiting embodiments of the present disclosure are further directed to a kit that includes one or more of any of the sleeves described herein above or otherwise contemplated herein in combination with one or more percutaneous devices for use therewith. The at least one percutaneous device has a first end and a second end; the second end of the at least one percutaneous device is designed for insertion through a skin and into a bone of a subject, and the first end is designed to extend above the skin of the subject.

The terms "percutaneous device" and "external fixation member" are used herein interchangeably and refer to any device that is capable of being fixated within a patient (i.e., capable of being inserted through the skin and tissue of a patient and into a bone thereof) and to which a distraction force may be applied. Non-limiting examples of percutaneous devices that may be utilized in accordance with the present disclosure include pins, screws, and wires. These percutaneous devices may be formed of metallic, polymeric, and/or biodegradable materials. In addition, at least a portion of the percutaneous devices is formed of a substantially rigid material.

In addition, the kit may further include one or more additional components and/or reagents that can be utilized with the assembly(ies) described or otherwise disclosed herein. For example, but not by way of limitation, the kit may further include a bonding material, an antimicrobial agent, and/or a wound healing agent. The bonding material and/or antimicrobial/wound healing agent may be applied to or otherwise associated with the sleeve(s) prior to disposal in the kit, or the bonding material and/or antimicrobial/ wound healing agent may be disposed in the kit separate from the sleeve(s) (such as, but not limited to, in separate containers or compartments of the kit). Alternatively and/or in addition thereto, the kit may include one or more securing elements and/or alignment elements as described herein above for addition to a sleeve present in the kit. Further, the kit may include an Allen wrench or other device that can be utilized to releasably or permanently secure a sleeve to a percutaneous device as well any device that can be utilized to align/orient the sleeve in the appropriate direction of migration.

The relative numbers and amounts of sleeves, percutaneous devices, and/or additional components/reagents present in the kit can vary widely. Also, when multiple sleeves are present, the sleeves may have the same shape and/or size, or the sleeves may have different shapes and/or sizes. Likewise, when multiple percutaneous devices are present, the percutaneous devices may have the same shape and/or size, or the percutaneous devices may have different shapes and/or sizes. In addition, the kit can further include a set of written instructions explaining how to use the kit. A kit of this nature can be used in any of the methods described or otherwise contemplated herein.

Certain non-limiting embodiments of the present disclosure are further directed to a system that includes any of the sleeves disclosed or otherwise contemplated herein in combination with any of the percutaneous devices described or otherwise contemplated herein.

Certain non-limiting embodiments of the present disclosure are further directed to an assembly that includes any of the sleeves described or otherwise contemplated herein in combination with any of the percutaneous devices described or otherwise contemplated herein, wherein the sleeve is disposed over the first end of the percutaneous device such that at least a portion of the percutaneous device is positioned in the interior receiving space of the sleeve body.

In certain non-limiting embodiments, the sleeve is releasably or permanently secured about the percutaneous device.

In certain non-limiting embodiments, the sleeve does not extend to the second end of the percutaneous device.

In certain non-limiting embodiments, the upper end of the sleeve body is closed, and the first end of the percutaneous device is disposed within the sleeve body. In other non-limiting embodiments, the upper end of the sleeve body is open, and the first end of the percutaneous device extends above the open upper end of the sleeve body.

Certain non-limiting embodiments of the present disclosure are directed to a method of reducing tension in a skin of a patient following placement of a percutaneous device therein. The method includes the steps of inserting at least one of any of the percutaneous devices described or otherwise contemplated herein through the skin of the patient and into a bone of the patient; positioning any of the sleeves described or otherwise contemplated herein about the percutaneous device, such that at least a portion of the percutaneous device is disposed through the open lower end of the sleeve body and into at least a portion of the interior receiving space of the sleeve body of the sleeve, and wherein the cutting edge of the sleeve is positioned in contact with the skin adjacent to the percutaneous device; and releasably or permanently securing the sleeve in position about the percutaneous device.

In this manner, the cutting edge of the sleeve functions, at a minimum, to reduce pressure on the skin and soft tissue surrounding the insertion site during patient movement, healing, and/or distraction, thereby reducing the risk of infection.

In certain non-limiting embodiments, the lower end of the sleeve does not contact the bone into which the percutaneous device is inserted.

When the sleeve includes an alignment element, the method may further include the step of aligning/orienting the cutting edge of the sleeve to substantially correspond to a primary anticipated direction of migration of the percutaneous device using the alignment element. The method may further include one or more subsequent steps of realigning/reorienting the cutting edge of the sleeve in the primary anticipated direction of migration, as needed.

Figure 1:
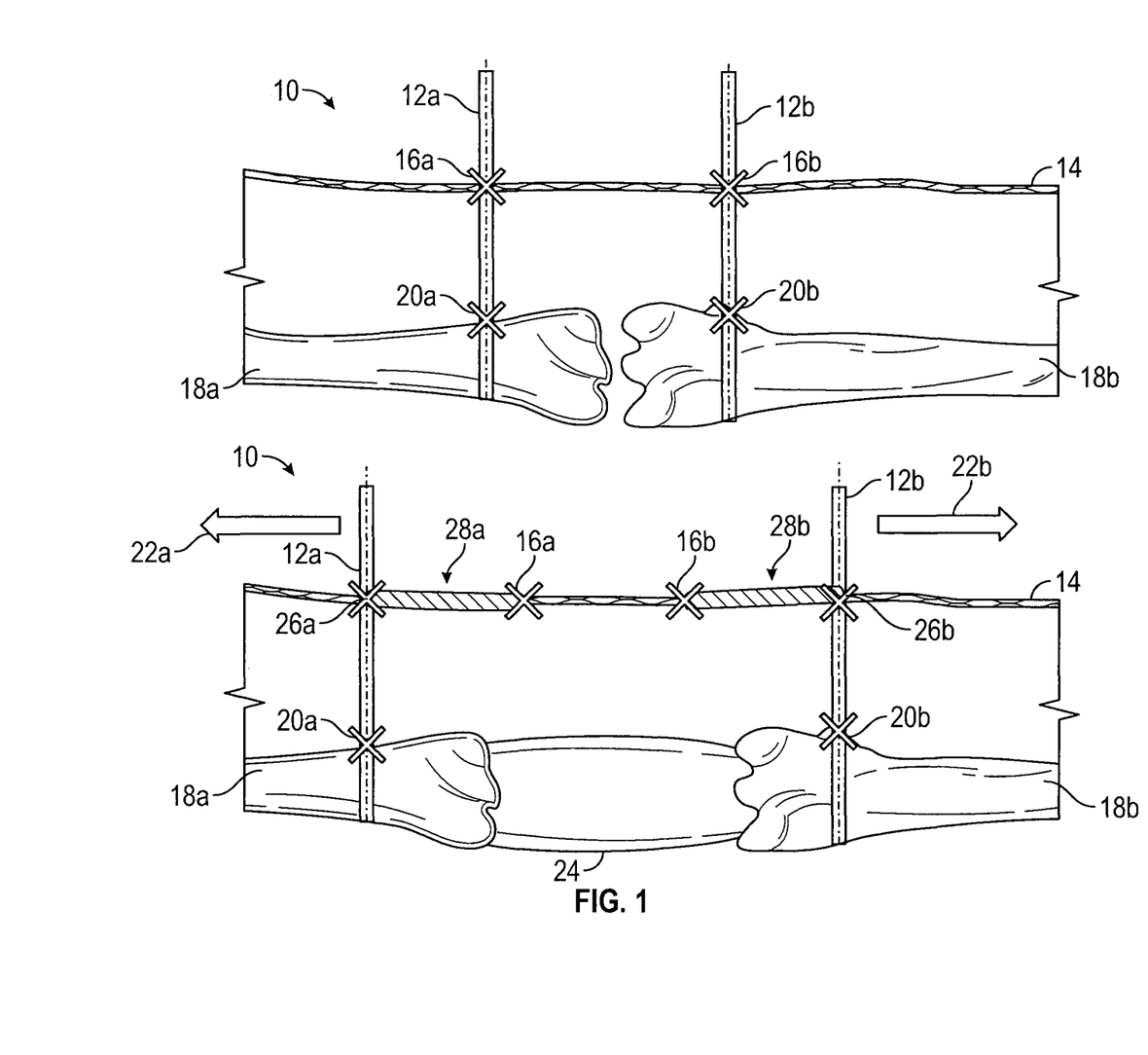
FIG. 1 contains diagrammatic views of the use of a prior art external fixation device and creation of pin tracts during a bone distraction procedure.

Turning now to the Drawings, FIG. 1 illustrates the use of a prior art external fixation system 10 and creation of pin tracts 28 during bone distraction. As shown in the upper panel, two percutaneous devices 12a and 12b are inserted through a skin 14 of a patient at insertions sites 16a and 16b, respectively, and further inserted into a bone that has been partially or completely separated. That is, the external fixation members 12a and 12b are inserted through the skin insertions sites 16a and 16b, respectively, and into two segments 18a and 18b, respectively, of the cut/separated bone of the patient at insertions sites 20a and 20b, respectively.

As shown in the lower panel of FIG. 1, during distraction osteogenesis, a distraction force is applied to each of the external fixation members 12a and 12b in directions 22a and 22b, respectively, so as to slowly pull the two bone segments 18a and 18b, respectively, apart. As the bone segments 18a and 18b are pulled apart, osteogenesis occurs, and new bone 24 is formed in the gap produced by the distraction forces, thus rejoining the bone segments 18a and 18b. In distraction osteogenesis, the distraction forces are applied slowly over time, so as to allow the new bone 24 to grow and harden over time. Typically, this process takes a period of time in a range of from about one month to about six months, such as (but not limited to) about one month, about six weeks, about two months, about three months, about four months, about five months, or about six months, or any other range between two of these values, or even longer, depending on the process.

However, as the distraction forces pull the two bone segments 18a and 18b apart, the percutaneous devices 12a and 12b move through the skin 14 and cut the skin 14 in the process. That is, an area 26a of the skin 14 around the leading edge of the external fixation member 12a is stretched until the skin 14 cuts or tears and forms a pin tract 28a. Likewise, an area 26b of the skin 14 around the leading edge of the external fixation member 12b is stretched until the skin 14 cuts or tears and forms a pin tract 28b. As stated above, these pin tracts 28a and 28b are highly prone to infection that can potentially have a devastating effect on the success of the distraction osteogenesis (or any other external fixation procedures in which pin tracts can be formed).

Therefore, the present disclosure is directed to sleeves, kits, assemblies, and methods that reduce skin tension and thus reduce the risk of pin tract infection, thereby overcoming the defects and disadvantages of the prior art systems. This is accomplished by minimizing the cutting of the skin and thereby controlling the incidence (and/or length) of pin tracts being formed in the skin. One non-limiting embodiment of these systems and methods will now be described with reference to FIGS. 2-6.

Figure 2:
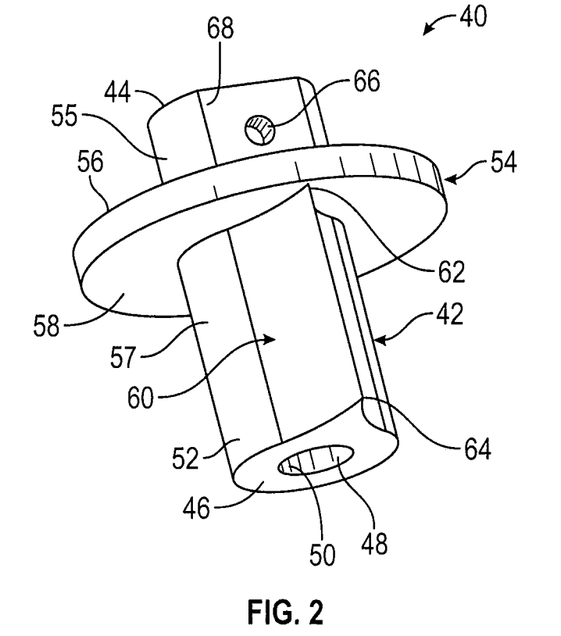
FIG. 2 is a first perspective view of a first embodiment of a sleeve for a percutaneous device constructed in accordance with the present disclosure.
Figure 3:
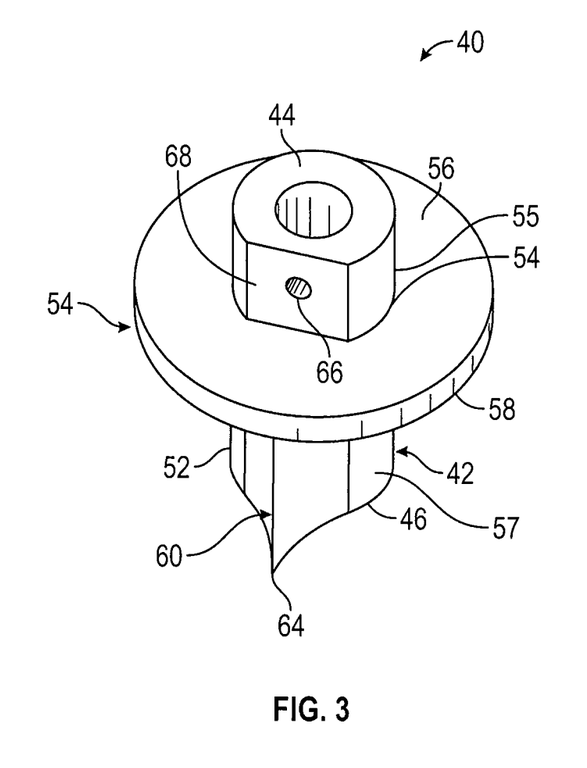
FIG. 3 is a second perspective view of the sleeve of FIG. 2.
Figure 4:
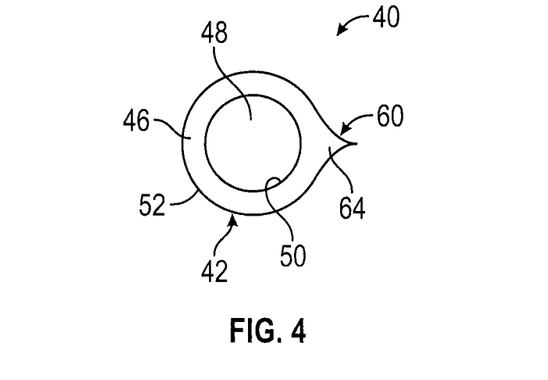
FIG. 4 is a bottom plan view of the sleeve of FIGS. 2-3.

In this embodiment of the present disclosure, and as shown in FIGS. 2-4, a sleeve 40 includes a sleeve body 42 that extends from an upper end 44 to an open lower end 46 thereof. As shown in FIGS. 2 and 4, the sleeve body 42 includes a recess that extends into and at least partially through the sleeve body 42 from the open lower end 46 thereof toward the upper end 44 thereof. As such, the recess defines an interior receiving space 48 that is designed for receiving a portion of a percutaneous device within at least a portion thereof.

The sleeve body 42 also includes an inner surface 50 and an outer surface 52. The inner and outer surfaces 50 and 52 of the sleeve body 42 may possess any shape and dimension that allows the sleeve 40 to function in accordance with the present disclosure. In one non-limiting example, the sleeve body 42 is shown in FIGS. 2-6 as having a substantially tubular (cylindrical) shape; however, it will be understood that the sleeve body 42 may possess any other shapes so long as the sleeve body 42 possesses the interior receiving space 48 that is dimensioned to receive and hold a portion of a percutaneous device. For example, the inner surface 50 and/or the outer surface 52 of the sleeve body 42 may have one or more shapes such as (but not limited to), cylindrical, conical, frustoconical, pyramidal, frustopyramidal, cuboidal, or prismatic (including a prism of any number of sides, such as (but not limited to) a triangular prism, a hexagonal prism, an octagonal prism, etc.), and the like. In addition, the inner surface 50 and the outer surface 52 may have the same shape, or the inner surface 50 and the outer surface 52 may have different shapes.

The inner surface 50 of the sleeve body 42 may include an engagement element for ensuring proper placement of the percutaneous device within the interior receiving space 48 of the sleeve body 42. For example (but not by way of limitation), the inner surface 50 of the sleeve body 42 may be provided with threading that functions as the engagement element and that ensures proper placement of the sleeve 40 on the percutaneous device. Alternatively, the percutaneous device may simply slidably engage the inner surface 50 of the sleeve body 42. In certain non-limiting embodiments, the engagement element may also serve as a securing element for maintaining appropriate positioning of the sleeve 40 on the percutaneous device; alternatively, the sleeve 40 may be provided with another element that functions as a securing element, as described in greater detail herein below.

The sleeve 40 also includes a flange 54 that has an upper surface 56 and a lower surface 58. The flange 54 extends at a substantially perpendicular angle from the outer surface 52 of the sleeve body 42 above the lower end 46 of the sleeve body 42. The flange 54 is also designed to extend in a direction substantially parallel to the patient's skin and is designed to be disposed upon a surface of the patient's skin when the sleeve 40 is disposed about a percutaneous device that is inserted through the patient's skin and into the patient's bone. This configuration allows the flange 54 to serve as a guard that reduces the risk of infection by substantially protecting the percutaneous device insertion site on the surface of the skin from exposure to microorganisms (as the ability of microorganisms to penetrate into the insertion site is reduced).

The flange 54 may have any shape that allows the flange to function as described herein. For example, the flange 54 may be provided with a substantially tubular (cylindrical) or torus shape, as shown, or the flange 54 may have one or more shapes such as (but not limited to), cylindrical, conical, frustoconical, pyramidal, frustopyramidal, cuboidal, or prismatic (including a prism of any number of sides, such as (but not limited to) a triangular prism, a hexagonal prism, an octagonal prism, etc.), and the like.

FIGS. 2-6 depict the flange 54 as separating the sleeve body 42 into an upper portion 55 and a lower portion 57. However, it will be understood that this positioning of the flange 54 in relation to the sleeve body 42 is for purposes of example only; if desired, the flange 54 may extend substantially to the upper end 44 of the sleeve body 42.

The sleeve 40 further includes a cutting edge 60 that has an upper end 62 and a lower end 64. The cutting edge 60 extends from a portion of the outer surface 52 of the sleeve body 42 below the flange 54 such that the upper end 62 of the cutting edge 60 is substantially in contact with the lower surface 58 of the flange 54. The cutting edge 60 is designed for placement in contact with the patient's skin that is adjacent to the percutaneous device when the sleeve 40 is positioned about the percutaneous device. In this manner, the cutting edge 60 defines a leading edge of the sleeve 40/percutaneous device assembly in a primary anticipated direction of migration of the assembly.

It will be understood that the cutting edge 60 may assume any shape that allows the cutting edge to function in accordance with the present disclosure. For example (but not by way of limitation), the cutting edge 60 may simply be a blade that extends at an angle from the outer surface 52 of the sleeve body 42. In another non-limiting example, the cutting edge 60 may assume a substantially pyramidal or triangular prism shape. In another non-limiting example (and as shown in FIG. 2), the cutting edge 60 may be formed of two concave sections that each extend from the outer surface 52 of the sleeve body 42 on one end and that are attached to each other on the other ends thereof to form the sharp, knife-like edge. However, it is to be understood that the particular structure of the cutting edge 60 depicted in FIG. 2 should not be construed as limiting; the cutting edge 60 may be formed of two sections that have any shape(s) (such as, but not limited to, straight or convex shape(s)), so long as these two sections extend from the outer surface 52 of the sleeve body 42 on one end and are attached to each other on the other end to form the sharp, knife-like edge. In addition, other structures that include more than two sides can be utilized for the cutting edge, so long as a sharp, knife-like edge is formed so that the cutting edge can function in accordance with the present disclosure.

By positioning the flange 54 immediately above and in contact with the cutting edge 60, the flange 54 functions as a guard to: (1) substantially protect the cutting edge 60 and the percutaneous device insertion site on the surface of the skin from exposure to microorganisms (as the ability of microorganisms to penetrate into the insertion site is reduced); (2) reduce the risk of injury to medical personnel during placement of the sleeve/percutaneous device assembly; and (3) reduce the risk of injury to the patient and/or medical personnel during the extended period of time that the assembly is in place.

The flange 54 may cover at least a portion of the upper end 62 of the cutting edge 60, or the flange 54 may cover all of the upper end 62 of the cutting edge 60. For example (but not by way of limitation), an outer edge of the flange 54 may extend beyond the cutting edge 60, if desired.

Each of the upper end 44 and lower end 46 of the sleeve body 42, the upper surface 56 and lower surface 58 of the flange 54, and the upper end 62 and lower end 64 of the cutting edge 60 may be provided with any shape/configuration, so long as the sleeve 40 is capable of functioning in accordance with the present disclosure. For example, but not by way of limitation, each of these ends/surfaces may have a shape that is independently selected from a substantially planar shape, a substantially convex shape, and a substantially concave shape. The shapes of the ends/surfaces may be selected, for example (but not by way of limitation) based upon any patient structures or other device structures that the ends/surfaces encounter.

As shown in FIG. 3, the upper end 44 of the sleeve body 42 may be open such that the interior receiving space 48 extends from the lower end 46 to the upper end 44 thereof; this configuration will allow a percutaneous device to extend above the open upper end 44 of the sleeve body 42 and thus extend through the sleeve 40, is desired. In addition, the positioning of the sleeve 40 can be adjusted to various heights on the percutaneous device, thus providing another advantage of the present system and methods over the prior art. Alternatively, the upper end 44 of the sleeve body 42 may be closed, such that the interior receiving space 48 does not extend from the lower end 46 to the upper end 44 thereof. In this configuration, the sleeve 40 essentially acts as a cap that is disposed on the upper end of the percutaneous device; in addition, this configuration will require that the height of the portion of the percutaneous device that extends above the skin of the patient be less than (or substantially similar to) the distance between the lower surface 58 of the flange 54 and the upper end 44 of the sleeve body 42 of the sleeve 40.

The portion of the outer surface 52 of the sleeve body 42 opposite the cutting edge 60 (as well as any portions of the cutting edge 60 other than the knife-like edge, if formed of multiple sections as described herein above) may be provided with any configuration that allows the sleeve 40 to function as described herein. In one non-limiting embodiment, said portion of the outer surface 52 (and/or the sections of the cutting edge 60 other than the knife-like edge) may be provided with a shape (such as, but not limited to, a substantially elliptical shape, a substantially concave shape, or a substantially convex shape) that eases the skin back together following cutting by the cutting edge 60, thus aiding the incision in resolving/closing itself naturally.

The sleeve 40 may further be provided with a securing element 66 that aids in releasably or permanently securing the sleeve 40 to a percutaneous device. For example (but not by way of limitation), in FIGS. 2-3, the sleeve 40 is depicted as having a securing element 66 that includes a threaded recess formed in the outer surface 52 of the sleeve body 42 above the flange 54 and a set screw inserted into the threaded recess; this embodiment of the securing element 66 can be utilized to releasably or permanently secure the percutaneous device to the sleeve 40 via the use of existing tools, such as (but not limited to), an Allen wrench. However, the use of the threaded recess/set screw is for purposes of example only, and it will be understood that any other mechanisms of securing the sleeve 40 to the percutaneous device that are known to a person having ordinary skill in the art or otherwise contemplated herein will also fall within the scope of the term "securing element," as used herein. Other examples of structural features that can function as securing elements include (but are not limited to) any type of vise or clamp-like structures or other actuatable structures that can interact with a portion of the percutaneous device and maintain said device in a secured position. Further examples of structural features that can function as securing elements will be readily apparent to a person having ordinary skill in the art, and thus no further explanation thereof is deemed necessary.

In addition, the securing element 66 may permanently secure the sleeve 40 to the percutaneous device, or the securing element 66 may releasably secure the sleeve 40 to the percutaneous device and thus allow for multiple adjustments of the sleeve 40 on the percutaneous device and/or subsequent removal of the sleeve 40 from the percutaneous device.

The sleeve 40 may also be provided with an alignment element 68 that indicates the direction and positioning of the cutting edge 60. Upon placement of the sleeve 40 upon the percutaneous device and positioning of the assembly through/within a patient's skin, the cutting edge 60 will not be visible because of the flange 54 and the skin of the patient. Therefore, the alignment element 68 provides a visual confirmation of the direction in which the cutting edge 60 is positioned. In certain non-limiting embodiments, the securing element 66 can also function as an alignment element 68 when the securing element is positioned in alignment with the cutting edge 60. Alternatively (and/or in addition thereto), the sleeve 40 may be provided with other feature(s) that assist in aligning/orienting the cutting edge 60 in the proper direction and thus function as the alignment element 68. For example (but not by way of limitation), the sleeve 40 is illustrated in FIGS. 2-3 as being further provided with a flat surface on a portion of the outer surface 52 of the sleeve body 42 above the flange 54, wherein the flat surface is substantially in alignment with the cutting edge 60. In this manner, the flat surface (or the flat surface in combination with the securing element 66) functions as the alignment element 68. Optionally, a portion of the outer surface 52 of the sleeve body 42 above the flange 54 and/or a portion of the upper surface 56 of the flange 54 may have printing, embossing, etching, etc. thereon that functions as the alignment element 68 by indicating the position and direction of the cutting edge 60. In another optional embodiment, one or more indented and/or raised portions may be present on the outer surface 52 of the sleeve body 42 above the flange 54 and/or on the upper surface 56 of the flange 54 that function as the alignment element 68 and thus indicate the position and direction of the cutting edge 60; in one particular (but non-limiting) example, an indented or raised portion may be present on the upper surface 56 of the flange 54 that functions as the alignment element 68 by outlining the actual structure of the cutting edge 66 that rests below the flange 54. Other examples of structural features that can function as alignment elements will be readily apparent to a person having ordinary skill in the art, and thus no further explanation thereof is deemed necessary.

The individual portions (i.e., sleeve body 42, flange 54, and cutting edge 60) of the sleeve 40 may be formed of any material(s) that will allow the sleeve to function in accordance with the present disclosure. In certain non-limiting embodiments, at least a portion of the sleeve 40 is formed of at least one substantially rigid material, such as (but not limited to) a metallic and/or polymeric material. In certain non-limiting embodiments, at least two of the components of the sleeve 40 (i.e., the sleeve body 42, the flange 54, and the cutting edge 60) are integrally formed of the same material. In a particular (but non-limiting) embodiment, all three components of the sleeve 40 are integrally formed of the same material. In an alternative embodiment, at least two or all three components of the sleeve 40 (i.e., the sleeve body 42, the flange 54, and the cutting edge 60) are each formed of different materials.

Any portions of the sleeve 40 (such as, but not limited to, the sleeve body 42, flange 54, and cutting edge 60) may have at least one antimicrobial agent (as described in detail herein above or otherwise contemplated herein) disposed on at least a portion thereof. For example (but not by way of limitation), a portion of the cutting edge 60 of the sleeve 40 may have an antimicrobial agent associated with at least a portion of a surface thereof, so that the skin of the patient is contacted with an antimicrobial agent during the cutting process. Alternatively (and/or in addition thereto), a portion of the sleeve body 42 below the flange 54 of the sleeve 40 may have an antimicrobial agent associated with at least a portion of a surface thereof, so that the skin of the patient comes into contact with an antimicrobial agent following cutting of the skin by the cutting edge 60.

Figure 5:
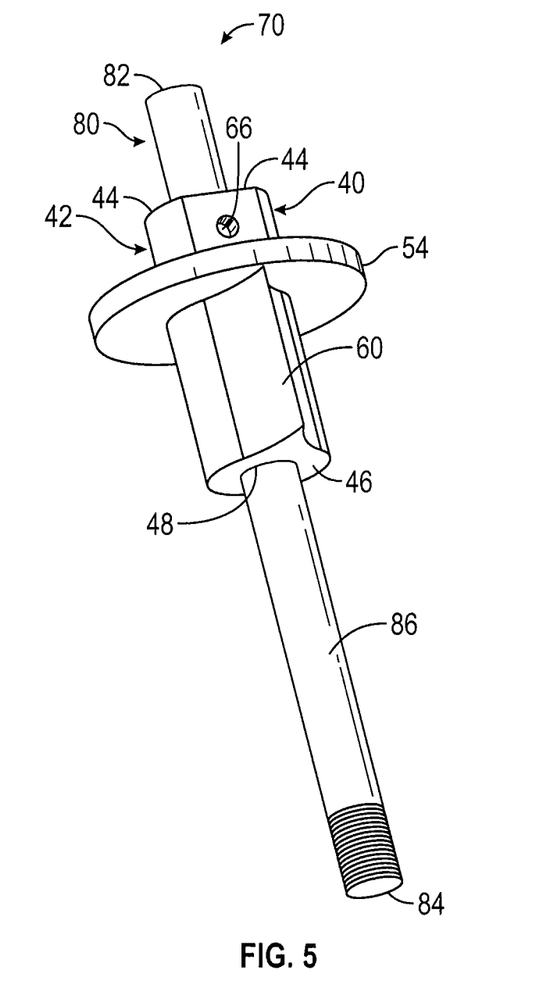
FIG. 5 is a perspective view of an assembly of the present disclosure, wherein the assembly includes the sleeve of FIGS. 2-4 disposed on a percutaneous device.

FIG. 5 illustrates an assembly 70 that is formed when the sleeve 40 of FIGS. 2-4 is positioned on a percutaneous device 80. Percutaneous devices useful for various orthopedic procedures are well known in the art, and thus the percutaneous device 80 may be any existing percutaneous device known in the art or otherwise as contemplated herein. As shown in FIG. 5, the percutaneous device 80 has a first end 82, a second end 84, and an outer surface 86. The second end 84 of the percutaneous device 80 is designed for insertion through a patient's skin and into a bone of the patient. The first end 82 of the percutaneous device 80 is designed to extend above the patient's skin. To form the assembly 70, the first end 82 of the percutaneous device 80 is inserted through the lower end 46 of the sleeve body 42 of the sleeve 40 so that a portion of the percutaneous device 80 is disposed in the interior receiving space 48 of the sleeve body 42 of the sleeve 40. When the upper end 44 of the sleeve body 42 of the sleeve 40 is open, as shown in FIG. 5, the first end 82 of the percutaneous device 80 extends through the open upper end 44 of the sleeve body 42 of the sleeve 40; this allows the sleeve 40 to be adjusted to various positions on the percutaneous device 80. The sleeve 40 can subsequently be secured in the desired position on the percutaneous device 80 using the securing element 66. The sleeve 40 can be permanently secured or releasably secured about the percutaneous device 80 and adjusted and aligned (and readjusted and realigned) as necessary, as described in detail herein above.

Figure 6:
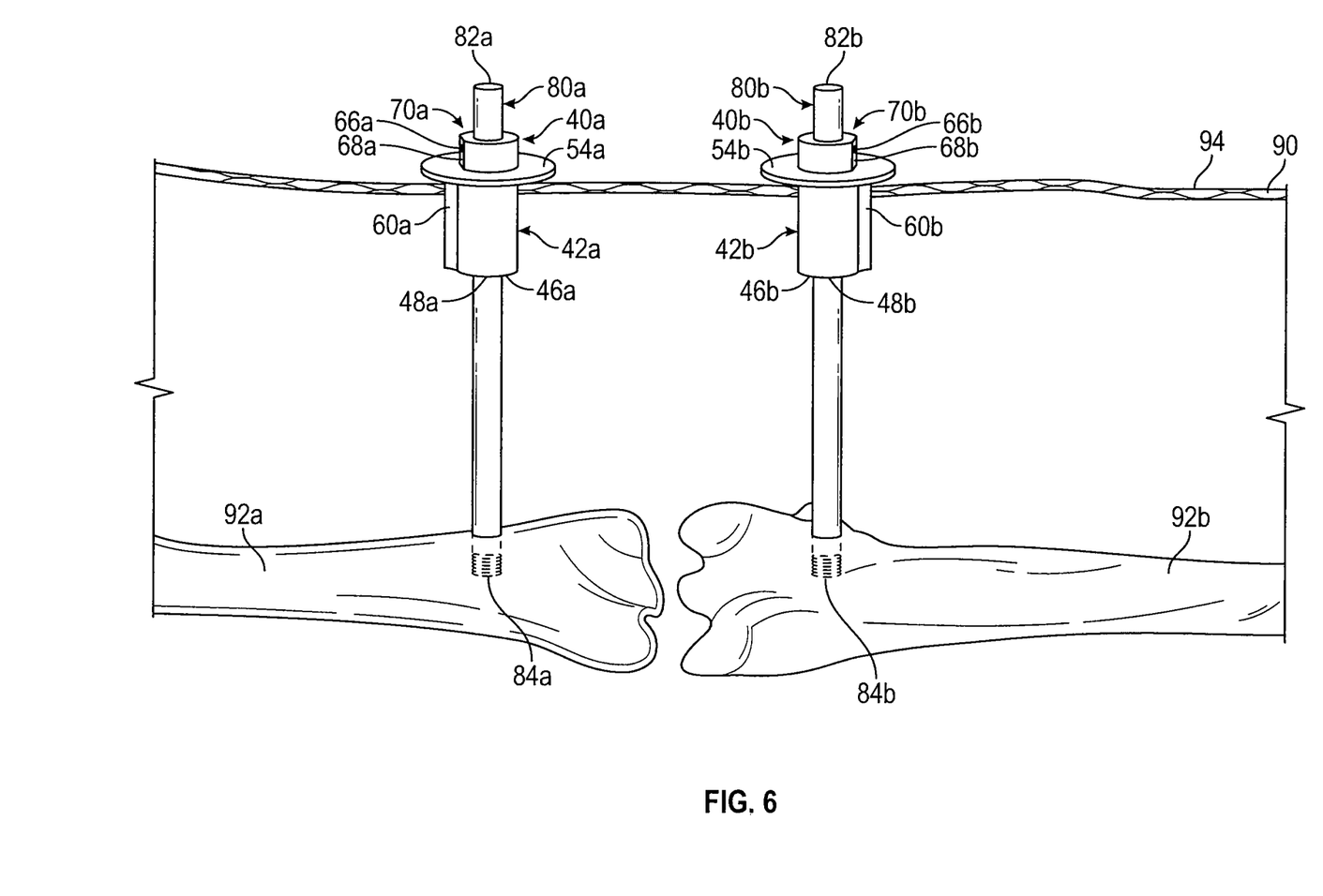
FIG. 6 contains a diagrammatic view of two of the sleeve/percutaneous device assemblies of FIG. 5, each inserted through the skin and into a bone segment of a patient.

FIG. 6 illustrates placement of two of the assemblies 70 of FIG. 5 within a patient (the two assemblies being designated as assembly 70a and assembly 70b in FIG. 6). In the method, a second end 84a of a percutaneous device 80a is inserted through a skin 90 of a patient and further inserted into a bone segment 92a of the patient; likewise, a second end 84b of a percutaneous device 80b is inserted through the skin 90 of the patient and further inserted into a bone segment 92b of the patient. A sleeve 40a is then disposed about the percutaneous device 80a via the methods described herein above or otherwise contemplated herein, while a sleeve 40b is then disposed about the percutaneous device 80b in the same manner. Each of the sleeves 40a/40b may be independently disposed about the corresponding percutaneous device 80a/80b prior to insertion of the percutaneous device 80a/80b into the skin 90 of patient; alternatively, each of the assemblies 70a/70b may first be formed, and then the percutaneous device 80a/80b of the assembly 70a/70b is inserted through the skin 90 and into the bone segment 92a/92b of the patient.

During placement of each of the sleeves 40a/40b about the corresponding percutaneous device 80a/80b, at least a portion of the percutaneous device 80a/80b is disposed through the open lower end 46a/46b of the sleeve body 42a/42b of the sleeve 40a/40b and into at least a portion of the interior receiving space 48a/48b of the sleeve body 42a/42b of the sleeve 40a/40b. Regardless of whether or not each of the sleeves 40a/40b is disposed about the corresponding percutaneous device 80a/80b before or after insertion of the percutaneous device 80a/80b into the patient, the placement of each of the sleeves 40a/40b on the percutaneous device 80a/80b is subsequently varied until the flange 54a/54b is disposed upon an upper surface 94 of the skin 90 so that the cutting edge 60a/60b of each of the sleeves 40a/40b is positioned in contact with the skin 90 adjacent to the corresponding percutaneous device 80a/80b. Once the proper positioning is obtained, each of the sleeves 40a/40b is releasably secured in position about the corresponding percutaneous device 80a/80b (and in proper positioning with the skin 90 of the patient) via the securing element 66a/66b. In addition, the alignment element 68a/68b of each of the sleeves 40a/40b may be utilized to ensure that the cutting edge 60a/60b of each of the sleeves 40a/40b is aligned and/or oriented in the proper direction. As noted in FIG. 6, the cutting edge 60a is aligned in the opposing direction to the cutting edge 60b; these opposing directions indicate the primary anticipated directions of migration of the percutaneous devices 80a and 80b, respectively, based on the distraction forces to be applied thereto.

During distraction, if the alignment element 68a/68b is no longer aligned/oriented in the primary direction of migration, then the securing element 66a/66b can be sufficiently released so that the positioning of the sleeve 40a/40b on the percutaneous device 80a/80b in a substantially horizontal plane (or yaw axis) can be varied until the alignment element 68a/68b is aligned/oriented in the primary direction of migration. Then the securing element 66a/66b can be utilized to once again releasably secure the sleeve 40a/40b in position about the percutaneous device 80a/80b.

Various embodiments of the sleeve 40 (including, but not limited to, sleeves 40a and 40b) may be provided with multiple lengths, widths, and/or heights, depending on the type, length, width, and height of the percutaneous device 80 (including, but not limited to, percutaneous devices 80a and 80b) utilized, the particular insertion site in the patient, the various anatomical structures around the insertion site and/or between the insertion site and the bone 92 in which the percutaneous device 80 will be inserted, and the like. The percutaneous device 80 may also be provided with multiple lengths, widths, and/or heights, as are well known in the art, depending on the particular use of the percutaneous device 80. As such, the selection of a particular length, width, and height for the sleeve 40 and a particular length, width, and height for the percutaneous device 80 will be readily apparent to a person having ordinary skill in the art, and as such, no further description thereof is deemed necessary.

In addition, when the upper end 44 of the sleeve body 42 is open, the positioning of the sleeve 40 on the percutaneous device 80 can be varied (in both horizontal and vertical directions), both prior to and after placement of the percutaneous device 80 in the patient. For example (but not by way of limitation), it may be desirable to adjust (and potentially readjust) the placement of the sleeve 40 on the percutaneous device 80 in a substantially vertical direction during distraction osteogenesis or healing (or even in response to patient movement) based on the surface of the skin and/or the anatomical structures being traversed (or the anatomical structures in close proximity to the migration path); likewise, it may be desirable to readjust and/or reorient the positioning of the cutting edge 60 of the sleeve 40 in response to any changes in the primary direction of migration. For example (but not by way of limitation), the positioning of the cutting edge 60 of the sleeve 40 may be readjusted in response to gravity and/or movement so that the cutting edge 60 is reoriented in the current direction of migration.

Further, the sleeve 40 will be positioned on the percutaneous device 80 such that the sleeve 40 does not extend to the second end 84 of the percutaneous device 80 (as the second end 84 of the percutaneous device 80 must extend into the bone 92 of the patient). More particularly, the sleeve 40 will typically be positioned on the percutaneous device 80 such that the lower end 64 of the cutting edge 60 of the sleeve 40 does not contact the bone 92 into which the percutaneous device 80 is inserted. However, the lower end 64 of the cutting edge 60 of the sleeve 40 may be positioned at any point on the percutaneous device 80 between the skin 90 and the bone 92 through which the percutaneous device 80 is inserted. Selection of this positioning will be readily apparent to a person having ordinary skill in the art, based on various factors such as (but not limited to) the soft tissue structures encountered in between the skin and bone.

While FIG. 6 depicts the use of two assemblies of percutaneous devices/sleeves, it will be understood that any number of assemblies of percutaneous devices/sleeves may be utilized in accordance with the present disclosure. For example, the scope of the present disclosure includes the placement of a single assembly as well as the placement of three or more assemblies of percutaneous devices/sleeves.

Figure 7:
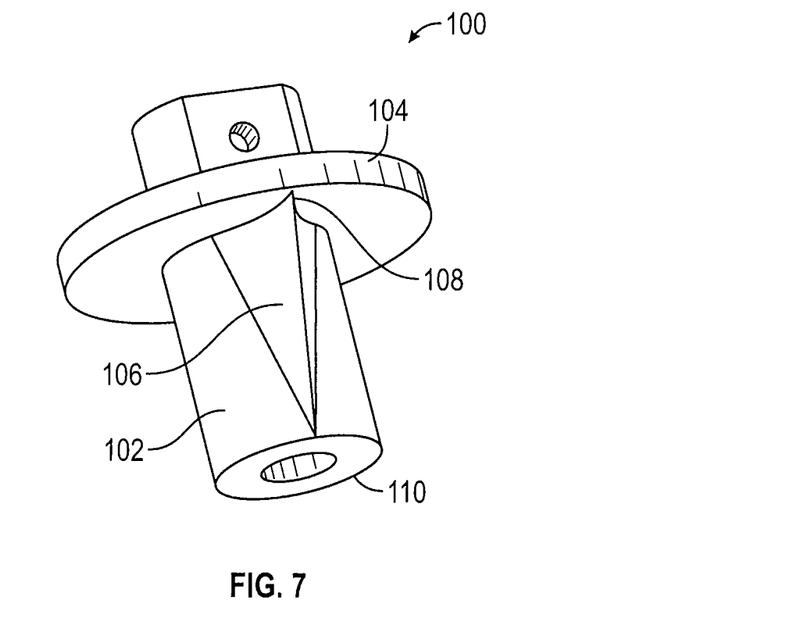
FIG. 7 is a perspective view of another embodiment of a sleeve for a percutaneous device constructed in accordance with the present disclosure.
Figure 8:
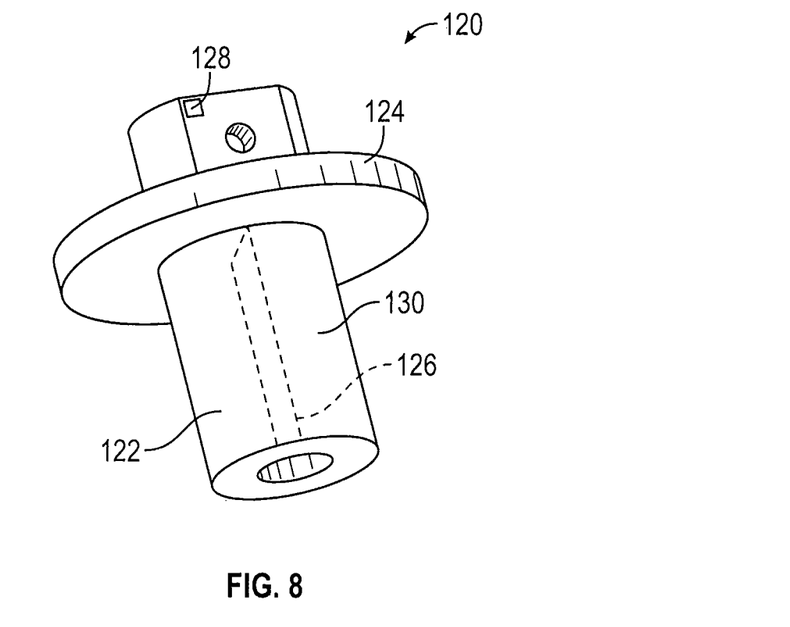
FIG. 8 is a perspective view of another embodiment of a sleeve for a percutaneous device constructed in accordance with the present disclosure.

FIGS. 7-8 illustrate other non-limiting embodiments of sleeves constructed in accordance with the present disclosure and that can function in the same manner as the sleeve 40 described herein above. FIG. 7 illustrates a sleeve 100 that has a sleeve body 102, a flange 104, and a cutting edge 106. The sleeve 100 is similar to the sleeve 40, except that a length of the cutting edge 106 decreases from an upper end 108 to a lower end 110 thereof. However, the structure shown in FIG. 7 should not be considered limiting; it will also be understood that this same effect can be achieved by decreasing the diameter of an outer surface of a sleeve rather than changing the actual length of the cutting edge, and as such, this embodiment also falls within the scope of the present disclosure.

FIG. 8 illustrates a sleeve 120 that has a sleeve body 122, a flange 124, and a cutting edge 126. The sleeve 120 is similar to the sleeve 40, except that the cutting edge 126 of the sleeve 120 is deployable, and as such, does not extend from an outer surface of the sleeve body 122 when not deployed (or only partially extends from the outer surface 122 when not deployed). In addition, the sleeve 120 has an actuator 128 that can be activated to deploy the cutting edge 126. This configuration of the sleeve 120 would allow the cutting edge 126 to be protected until the sleeve 120 is partially inserted into the skin of a patient, as described in detail herein above. In this manner, the cutting edge 126 can then be deployed after placement of the flange 124 of the sleeve 120 upon the skin of the patient, thereby protecting the medical personnel and patient from injury via accidental contact with the cutting edge 126. A deployable cutting edge 126 would also further reduce the risk of infection, as the cutting edge 126 would be protected from any inadvertent contact with bacteria during the placement process (such as, but not limited to, bacteria present on the skin's surface).

While the embodiments shown in the Drawings illustrate the systems of the present disclosure being utilized with external fixation in combination with distraction osteogenesis, it will be understood that the systems and methods disclosed herein are not limited to use with distraction osteogenesis. That is, as described herein above, pin tracts can be formed simply as the result of patient movement and/or healing when an external fixation system is in place, or even as a result of gravity or slight movement of the external fixation system. Therefore, the scope of the present disclosure explicitly includes devices, systems, and methods that can be utilized with any external fixation mechanisms known in the art or otherwise contemplated herein where pressure zones/pin tracts can potentially be formed and, as such, are at risk of infection.

Thus, in accordance with the present disclosure, there have been provided devices, assemblies, and kits, as well as methods of producing and using same, which fully satisfy the objectives and advantages set forth hereinabove. Although the present disclosure has been described in conjunction with the specific drawings, experimentation, results, and language set forth hereinabove, it is evident that many alternatives, modifications, and variations will be apparent to those skilled in the art. Accordingly, it is intended to embrace all such alternatives, modifications, and variations that fall within the spirit and broad scope of the present disclosure.

What is claimed is:

1. A sleeve for a percutaneous device, the sleeve comprising:
    a sleeve body having an upper end, an open lower end, an outer surface, an inner surface, and an interior receiving space that extends from the open lower end, the interior receiving space designed for receiving a portion of a percutaneous device within at least a portion thereof;
    a flange having an upper surface and a lower surface, wherein the flange extends at a substantially perpendicular angle from the outer surface of the sleeve body above the lower end thereof and that is designed to be disposed upon a surface of a skin of a patient; and
    a cutting edge having an upper end and a lower end, the cutting edge extending from a portion of the outer surface of the sleeve body below the flange such that the upper end of the cutting edge is substantially in contact with the lower surface of the flange, wherein the cutting edge is designed for placement in contact with the skin adjacent to the percutaneous device and defines a leading edge thereof in a primary anticipated direction of migration.

2. The sleeve of claim 1, wherein the sleeve is formed of at least one substantially rigid metallic and/or polymeric material.

3. The sleeve of claim 1, wherein the sleeve body, the flange, and the cutting edge are integrally formed of the same material.

4. The sleeve of claim 1, wherein at least two of the sleeve body, the flange, and the cutting edge are formed of different materials.

5. The sleeve of claim 1, wherein the sleeve body has a substantially tubular shape.

6. The sleeve of claim 1, wherein the upper end of the sleeve body is open such that a portion of the percutaneous device can extend above the upper end of the sleeve body and thus extend through the sleeve.

7. The sleeve of claim 1, wherein the lower surface of the flange covers at least a portion of the upper end of the cutting edge.

8. The sleeve of claim 1, wherein a profile of the cutting edge varies from the upper end to the lower end thereof.

9. The sleeve of claim 1, wherein the cutting edge is deployable, and wherein the sleeve further comprises an actuator for deploying the cutting edge.

10. The sleeve of claim 1, further comprising at least one of:
    a securing element for securing the sleeve to the percutaneous device;
    an alignment element for orienting the cutting edge in the primary anticipated direction of migration; and
    at least one agent disposed on at least a portion thereof.

11. The sleeve of claim 10, wherein the agent is selected from the group consisting of an antimicrobial agent, a wound healing agent, an anti-inflammatory agent, and combinations thereof.

12. A kit, comprising:
    at least one of the sleeves of claim 1; and
    at least one percutaneous device having a first end and a second end, wherein the second end of the at least one percutaneous device is designed for insertion through a skin and into a bone of a subject, and wherein the first end is designed to extend above the skin of the subject.

13. An assembly, comprising:
    a percutaneous device having a first end and a second end, wherein the second end of the percutaneous device is designed for insertion through a skin and into a bone of a subject, and wherein the first end is designed to extend above the skin of the subject; and
    a sleeve comprising:
        a sleeve body having an upper end, an open lower end, an outer surface, an inner surface, and an interior receiving space that extends from the open lower end, the interior receiving space designed for receiving a portion of a percutaneous device within at least a portion thereof;
        a flange having an upper surface and a lower surface, the flange extending at a substantially perpendicular angle from the outer surface of the sleeve body above the lower end thereof and that is designed to be disposed upon a surface of a skin of a patient; and
        a cutting edge having an upper end and a lower end, the cutting edge extending from a portion of the outer surface of the sleeve body below the flange such that the upper end of the cutting edge is substantially in contact with the lower surface of the flange, wherein the cutting edge is designed for placement in contact with the skin adjacent to the percutaneous device and defines a leading edge thereof in a primary anticipated direction of migration; and
    wherein the sleeve is disposed over the first end of the percutaneous device such that at least a portion of the percutaneous device is disposed in the interior receiving space of the sleeve body.

14. The assembly of claim 13, wherein the sleeve is secured about the percutaneous device.

15. The assembly of claim 13, wherein the sleeve does not extend to the second end of the percutaneous device.

16. The assembly of claim 13, wherein the sleeve is formed of at least one substantially rigid metallic and/or polymeric material.

17. The assembly of claim 13, wherein the sleeve body, the flange, and the cutting edge of the sleeve are integrally formed of the same material.

18. The assembly of claim 13, wherein at least two of the sleeve body, the flange, and the cutting edge of the sleeve are formed of different materials.

19. The assembly of claim 13, wherein the sleeve body has a substantially tubular shape.

20. The assembly of claim 13, wherein the upper end of the sleeve body is open, and the first end of the percutaneous device extends above the open upper end of the sleeve body.

21. The assembly of claim 13, wherein the lower surface of the flange covers at least a portion of the upper end of the cutting edge.

22. The assembly of claim 13, wherein a profile of the cutting edge of the sleeve varies from the upper end to the lower end thereof.

23. The assembly of claim 13, wherein the cutting edge of the sleeve is deployable, and wherein the sleeve further comprises an actuator for deploying the cutting edge.

24. The assembly of claim 13, wherein the sleeve further comprises at least one of:
- a securing element for securing the sleeve to the percutaneous device;
- an alignment element for orienting the cutting edge in the primary anticipated direction of migration; and
- at least one agent disposed on at least a portion thereof.

25. The assembly of claim 24, wherein the agent is selected from the group consisting of an antimicrobial agent, a wound healing agent, an anti-inflammatory agent, and combinations thereof.

26. A method of reducing tension in a skin of a patient following placement of a percutaneous device therein, the method comprising the steps of:
- Inserting a portion of at least one percutaneous device through the skin of the patient and into a bone of the patient;
- positioning a sleeve about the percutaneous device, the sleeve comprising:
  - a sleeve body having an upper end, an open lower end, an outer surface, an inner surface, and an interior receiving space that extends from the open lower end;
  - a flange having an upper surface and a lower surface, the flange extending at a substantially perpendicular angle from the outer surface of the sleeve body above the lower end thereof and that is designed to be disposed upon a surface of a skin of a patient; and
  - a cutting edge having an upper end and a lower end, the cutting edge extending from a portion of the outer surface of the sleeve body below the flange such that the upper end of the cutting edge is substantially in contact with the lower surface of the flange;
- wherein, during positioning of the sleeve about the percutaneous device, at least a portion of the percutaneous device is disposed through the open lower end of the sleeve body and into at least a portion of the interior receiving space thereof, and wherein the cutting edge of the sleeve is positioned in contact with the skin adjacent to the percutaneous device; and
- securing the sleeve about the percutaneous device.

27. The method of claim 26, wherein the sleeve further comprises an alignment element, and wherein the method further comprises the step of orienting the cutting edge of the sleeve to substantially correspond to a primary anticipated direction of migration using the alignment element.

28. The method of claim 26, wherein the lower end of the sleeve does not contact the bone into which the percutaneous device is inserted.

29. The method of claim 26, wherein the sleeve is formed of at least one substantially rigid metallic and/or polymeric material.

30. The method of claim 26, wherein the sleeve body, the flange, and the cutting edge of the sleeve are integrally formed of the same material.

31. The method of claim 26, wherein at least two of the sleeve body, the flange, and the cutting edge of the sleeve are formed of different materials.

32. The method of claim 26, wherein the sleeve body of the sleeve has a substantially tubular shape.

33. The method of claim 26, wherein the upper end of the sleeve body is open, and the first end of the percutaneous device extends above the open upper end of the sleeve body.

34. The method of claim 26, wherein the lower surface of the flange covers at least a portion of the upper end of the cutting edge.

35. The method of claim 26, wherein a profile of the cutting edge of the sleeve varies from the upper end to the lower end thereof.

36. The method of claim 26, wherein the cutting edge of the sleeve is deployable, and wherein the sleeve further comprises an actuator for deploying the cutting edge.

37. The method of claim 26, wherein the sleeve further comprises at least one of:
- a securing element that secures the sleeve to the percutaneous device; and
- at least one agent disposed on at least a portion of the sleeve.

38. The method of claim 37, wherein the agent is selected from the group consisting of an antimicrobial agent, a wound healing agent, an anti-inflammatory agent, and combinations thereof.

* * * * *